(12) United States Patent
Hilmersson

(10) Patent No.: US 11,471,060 B2
(45) Date of Patent: Oct. 18, 2022

(54) PRESSURE CATHETER AND GUIDE WIRE ASSEMBLY

(71) Applicant: CAVIS TECHNOLOGIES AB, Uppsala (SE)

(72) Inventor: Mats Hilmersson, Bromma (SE)

(73) Assignee: CAVIS TECHNOLOGIES AB, Uppsala (SE)

( * ) Notice: Subject to any disclaimer, the term of this patent is extended or adjusted under 35 U.S.C. 154(b) by 771 days.

(21) Appl. No.: 16/079,408

(22) PCT Filed: Nov. 10, 2016

(86) PCT No.: PCT/EP2016/077203
§ 371 (c)(1),
(2) Date: Aug. 23, 2018

(87) PCT Pub. No.: WO2017/144128
PCT Pub. Date: Aug. 31, 2017

(65) Prior Publication Data
US 2019/0008398 A1 Jan. 10, 2019

(30) Foreign Application Priority Data
Feb. 26, 2016 (SE) .................... 1650250-2

(51) Int. Cl.
| | | |
|---|---|---|
| *A61B 5/02* | (2006.01) | |
| *A61B 5/0215* | (2006.01) | |
| *A61B 5/00* | (2006.01) | |
| *A61M 25/09* | (2006.01) | |
| *A61M 25/00* | (2006.01) | |

(52) U.S. Cl.
CPC .......... *A61B 5/0215* (2013.01); *A61B 5/6852* (2013.01); *A61M 25/09* (2013.01);
(Continued)

(58) Field of Classification Search
CPC .... A61B 5/0215; A61B 5/6852; A61M 25/09; A61M 2025/0003; A61M 2025/09083; A61M 2025/09175; A61M 2025/0915
See application file for complete search history.

(56) References Cited

U.S. PATENT DOCUMENTS

| | | |
|---|---|---|
| 4,953,553 A | 9/1990 | Tremulis |
| 4,955,862 A | 9/1990 | Sepetka |
| (Continued) | | |

FOREIGN PATENT DOCUMENTS

| | | | | |
|---|---|---|---|---|
| WO | WO 2009/120679 A1 | 10/2009 | | |
| WO | WO-2009120679 A1 * | 10/2009 | .......... | A61L 33/0011 |

OTHER PUBLICATIONS

International Search Report, issued in PCT/EP2016/07/203, dated Feb. 3, 2017.
(Continued)

*Primary Examiner* — Andrey Shostak
(74) *Attorney, Agent, or Firm* — Birch, Stewart, Kolasch & Birch, LLP

(57) ABSTRACT

A catheter and guide wire assembly for measurement of blood pressure in a living body, including a tubular shaft, which is connected to a tubular extension, which is connected to a permeable helical coil, which has a distal end that is secured in a distal tip, and a core member, which is attached in a distal portion of the tubular shaft and extends through the tubular extension and the helical coil, and is secured in the distal tip. The catheter and guide wire assembly has an outer diameter of about 0.35 mm and an open, inner lumen, which includes the tubular shaft, the tubular extension, the helical coil, and the core member. The catheter and guide wire assembly has a total flow-resistance
(Continued)

index less than about $1.2 \times 10^6$ mm$^{-3}$, and more preferably less than about $1.0 \times 10^6$ mm$^{-3}$, and even more preferably less than about $0.7 \times 10^6$ mm$^{-3}$.

19 Claims, 1 Drawing Sheet

(52) U.S. Cl.
CPC ............... *A61M 2025/0003* (2013.01); *A61M 2025/09083* (2013.01)

(56) References Cited

U.S. PATENT DOCUMENTS

| | | | |
|---|---|---|---|
| 4,964,409 A * | 10/1990 | Tremulis | A61B 5/0215 600/434 |
| 5,322,508 A | 6/1994 | Viera | |
| 5,860,938 A | 1/1999 | Lafontaine et al. | |
| 9,138,565 B2 | 9/2015 | Schwager | |
| 2003/0100847 A1 * | 5/2003 | D'Aquanni | A61M 25/09 600/585 |
| 2007/0255145 A1 * | 11/2007 | Smith | A61B 5/0215 600/485 |
| 2012/0238872 A1 * | 9/2012 | Schwager | A61M 25/09 600/434 |
| 2015/0066131 A1 * | 3/2015 | Luong | A61F 2/95 623/1.11 |
| 2016/0158502 A1 * | 6/2016 | Kume | A61M 39/1011 604/510 |

OTHER PUBLICATIONS

Written Opinion of the International Searching Authority, issued in PCT/EP2016/077203, dated Feb. 3, 2017.

* cited by examiner

PRESSURE CATHETER AND GUIDE WIRE ASSEMBLY

FIELD OF THE INVENTION

The present invention relates generally to a catheter and guide wire assembly for intravascular measurements of blood pressure in a living body, and comprises a tubular shaft, whose distal end is secured to the proximal end of a tubular extension, whose distal end is secured to the proximal end of a helical coil, whose distal end is secured to a blunt tip, and a core member arranged in a distal portion of the tubular shaft and extending through the tubular extension and the helical coil, and into the blunt tip, wherein the dimensions and structural constitution of the catheter and guide wire assembly are designed to make the catheter and guide wire assembly a useful medical tool in percutaneous coronary interventions.

BACKGROUND OF THE INVENTION

Catheter and guide wire assemblies for blood pressure measurements in a living body are known. An example of such a catheter and guide wire assembly is disclosed in the U.S. Pat. Nos. 4,953,553 and 4,964,409 to Tremulis, wherein a guiding member is described, which comprises an elongated main hollow tubular member, a tubular extension secured to a distal end of the tubular member, a flexible body secured to the distal end of the tubular extension, and a core member, which is secured in the inner lumen of the main tubular member and extends through the tubular extension and into the flexible body. According to this disclosure, the transverse cross-sectional area of the core member disposed within the inner lumen of the main tubular member should be at least 10% less, and preferably at least 25% less, than the transverse cross-sectional area of the inner lumen of the main tubular member, to not impede the flow of fluid there through or impede the passage of fluid pressure pulses there through. However, as recognized and stated in the U.S. Pat. No. 5,860,938 to Lafontaine et al., blood pressure signals from a catheter and guide wire assembly designed according to the teaching of the aforementioned patents may be extremely damped; and instead the U.S. Pat. No. 5,860,938 discloses a guide wire having a central inner lumen, wherein the guide wire in one embodiment has an outer diameter of 0.35 mm and the inner central lumen has a diameter of 0.19 mm. Although a guide wire having these dimensions may provide a better passageway for fluid pressure signals, it is still associated with drawbacks, when used in medical practice, especially the very stiff distal region. The same problems are associated with the guide wires disclosed in the U.S. Pat. No. 9,138,565 to Schwager et. al. and the U.S. Pat. No. 5,322,508 to Viera, respectively.

In use, a catheter and guide wire assembly of this type is filled with a fluid, typically saline, to create a fluid line from the distal portion, which, via a permeable, distal member, e.g. a coil, is in fluid connection with blood, to the proximal end, which is connected to an external pressure transducer. The pressure transducer comprises a membrane, on which the blood pressure, via the fluid line, exerts a pressure, thereby causing a deflection of the membrane. The amount of deflection is converted to an electrical signal, the amplitude of which is converted to a pressure reading, which typically is displayed on a monitor or a similar device.

Here it should be mentioned and appreciated that the requirements on a catheter and guide wire assembly, which both should function as a pressure conductor and a guide wire for maneuvering in, for example, the coronary arteries, are both demanding and inherently incompatible; that is, the catheter and guide wire assembly should have a high torsional rigidity and a bending stiffness which preferably varies along the length of the catheter and guide wire assembly, and should at the same time provide a pressure transmission line which provides good signal characteristics. Therefore, although a catheter and guide wire assembly having an inner lumen should be a very useful and presumably economically appealing tool for measuring blood pressure in a living body, such devices have never been generally accepted by the medical community. Further, although the importance of providing a relatively large inner lumen has been at least partly recognized in the documents referred to above, there are still improvements to be made regarding the signal quality and reliability as a pressure conductor and/or regarding the mechanical handling characteristics of the catheter and guide wire assemblies disclosed in those references. One object of the present invention is therefore to provide a catheter and guide wire assembly whose mechanical handling characteristics matches or exceeds the mechanical characteristics of the catheter and guide wire assemblies known today and which, in use, provides blood pressure measurements, the reliability and accuracy of which match or exceed the reliability and accuracy of the catheter and guide wire assemblies known today.

There is, however, also a further requirement on a pressure catheter and guide wire assembly which has not been recognized in the prior art. The reason for measuring blood pressure is in this context typically associated with a so-called PCI procedure (where PCI stands for Percutaneous Coronary Intervention), during which a doctor, typically a cardiologist or a radiologist, feeds a deflated balloon, which is arranged on a guide wire or on a pressure catheter of the type which is the subject of the present invention, from the inguinal femoral artery or the radial artery up through blood vessels until it reaches the site of a blockage in the arteries. X-ray imaging is used to guide the pressure catheter through the coronary artery. At the blockage, the balloon is inflated to open the artery, thereby increasing blood flow. A stent is often placed at the site of the blockage to permanently open the artery. The severity of the blockage can before the commence of the PCI procedure have been diagnosed by a technique called FFR (Fractional Flow Reserve), which involves the measurement of blood pressure distal to the (suspected) blockage and measurement of aortic blood pressure. At least the distal measurement is carried out with the use of the pressure catheter connected to an external pressure transducer. When the PCI procedure has been completed, the result of the treatment is verified by a repeated FFR measurement. However, during the actual PCI procedure, when the blockage is opened, the pressure catheter has been disconnected from the external pressure transducer, thereby also removing the counter-pressure created by the fluid, typically saline, in the catheter lumen, whose proximal end, before the disconnection, was abutting the membrane in the external pressure transducer, as has been described above. As an effect, blood has now filled the catheter lumen. In order to carry out the verifying blood pressure measurement, this blood has to be flushed back, out of the catheter lumen, preferably by means of the same standard syringe (or at least the same type of syringe), which was used to fill the catheter lumen with saline in the first place. If this blood is not flushed out, i.e. if a doctor tries to measure blood pressure while blood is still contained in the inner lumen, the damping of the pressure waves transmitted through the blood and any minor rests of the original fluid, e.g. saline, is very significant, presumably about 70% reduction in amplitude of the phasic blood pressure signal, which is way too much to provide clinically valuable results.

The catheter and guide wire assemblies known in the prior art are not adapted to this flushing step which is part of a PCI procedure; and a further, equally or even more important object of the present invention is to provide a catheter and guide wire assembly which is easy to handle and allows efficient flushing of blood out of the catheter lumen.

SUMMARY OF THE INVENTION

The above-mentioned objects are achieved by the present invention according to the independent claim. Preferred embodiments are set forth in the dependent claims.

The present invention relates to a catheter and guide wire assembly comprising a tubular shaft, whose distal end is connected to the proximal end of a tubular extension, whose distal end is connected to the proximal end of a helical coil, whose distal end is connected to a tip, and a core member, which is secured in a distal portion of the tubular shaft and extends through the tubular extension and the helical coil, and is secured in the tip. The catheter and guide wire assembly is subdivided into a tip region, a distal region and a proximal region. The catheter and guide wire assembly has an outer maximal diameter of about 0.014 inch (0.35 mm), and the core member, which is a solid metal wire, preferably made from stainless steel, has a diameter of about 0.07 mm to about 0.19 mm, and more preferably from about 0.09 mm to about 0.16 mm, in the region of the tubular extension. In one embodiment of the invention, this provides the catheter and guide wire assembly with an inner lumen having a free cross-sectional area of about 0.053 $mm^2$ in a region proximally of the core member fixation in the tubular shaft, a cross-sectional area of about 0.033 $mm^2$ in the region of the tubular shaft which includes a core member section, and a cross-sectional area of about 0.046 $mm^2$ in the tubular extension region. However, as will be seen below, to design and characterize a catheter and guide wire assembly by providing internal cross-sectional areas or cross-section diameters for different length sections is neither efficient nor appropriate. Embodiments of the present catheter and guide wire assembly are instead characterized by having a low total flow-resistance index, which preferably is less than about $1.2 \times 10^6$ $mm^{-3}$, or more preferably less than about $1.0 \times 10^6$ $mm^{-3}$, or even more preferably less than about $0.7 \times 10^6$ $mm^{-3}$.

In preferred embodiments of a catheter and guide wire assembly according to the present invention, the walls of an inner lumen, comprised of a tubular shaft and a tubular extension, have an anti-thrombogenic surface, e.g. have been provided with a heparin coating, to prevent blood from forming clots and thereby facilitating or even enabling flushing of blood out of the catheter lumen, which is a mandatory step before measuring pressure in a PCI procedure.

In preferred embodiments of a catheter and guide wire assembly according to the present invention, the middle of the tip region should have a bending resistance of preferably 0.01 to 0.95 $Nmm^2$, or even more preferably 0.02 to 0.12 $Nmm^2$.

In preferred embodiments of a catheter and guide wire assembly according to the present invention, the distal end of the distal region should have a bending resistance of preferably 0.95 to 6 $Nmm^2$, or even more preferably 1 to 3 $Nmm^2$.

In preferred embodiments of a catheter and guide wire assembly according to the present invention, the proximal end of the distal region should have a bending resistance of preferably 3 to 13 $Nmm^2$, or even more preferably 5 to 8 $Nmm^2$.

In preferred embodiments of a catheter and guide wire assembly according to the present invention, the proximal region should have a bending resistance of preferably 65 to 124 $Nmm^2$, or even more preferably 95 to 110 $Nmm^2$.

DETAILED DESCRIPTION OF PREFERRED EMBODIMENTS

The present invention relates generally to a catheter and guide wire assembly comprising a tubular shaft, a tubular extension, a helical coil, a blunt tip, and a core member, which is secured in the tubular shaft and extends through the tubular extension and the coil, and is secured in the tip. The diameter of the core member can vary along its length, i.e. along the length of the catheter and guide wire assembly, but is less than the inner diameter of the tubular shaft and the inner diameter of the tubular extension, respectively, such that the catheter and guide wire assembly is provided with an open inner lumen. It can be seen in FIGS. 1 and 2 that the catheter and guide wire assembly is subdivided into a tip region A, a distal region B and a proximal region C. Such catheter and guide wire assemblies are conceptually known, but have failed to achieve market acceptance, presumably because of their poor performance; and, as already have been discussed above, the technical challenges are indeed high and complex and, at least partly, mutually incompatible. For example, high torqueability and thereby good steerability is a feature that is mandatory for this type of medical device. However, high torqueability requires a high torsional rigidity, which suggests the use of a solid guide wire, but that is in contradiction with the requirement of having a free, open inner lumen for blood pressure wave transmission. The inventors of the present invention have found that in particular the pressure transmission capacity is surprisingly sensitive to the effective hydraulic diameter of the inner lumen of the catheter and guide wire assembly. Further, as was indicated above, when a guide wire and catheter assembly of this type is used in a PCI procedure involving, e.g., a FFR measurement, there is a need to flush out blood which has entered into and at least partly filled the inner lumen during the period of time when the catheter and guide wire was disconnected from an external pressure transducer.

Figure 1:
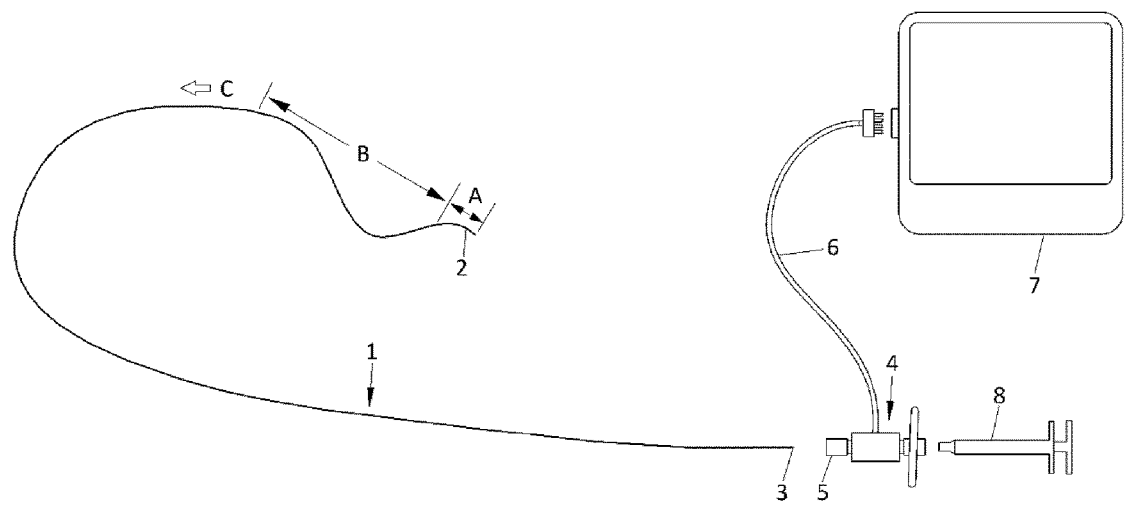
FIG. 1 shows a schematic view of the catheter and guide wire assembly according to the invention, which is connected to an external pressure transducer.

Below a pressure catheter and guide wire assembly according to the present invention will be described with reference to the appended drawings, wherein FIG. 1 schematically illustrates a pressure catheter and guide wire assembly 1, which has blood-permeable distal portion 2, an open, fluid-filled inner lumen and an open proximal end 3, and is connected to an external pressure transducer 4. The external pressure transducer 4, which is not part of the present invention, comprises a connector 5 and a connector cable 6, which is connectable to a monitor device 7. A syringe 8 is also connected to the pressure transducer. The external pressure transducer 4 contains a membrane and electric circuitry. When the catheter and guide wire assembly 1 has been connected to the connector 5, such that the open proximal end 3 of the catheter and guide wire assembly 1 abuts the membrane in the external pressure transducer 4, pressure waves can be transmitted through the fluid contained in the inner lumen of the catheter and guide wire 1 and cause deflections of the membrane. The electric circuitry in the external pressure transducer 4 converts these deflections into electric signals whose amplitudes correspond to the magnitudes of the pressure waves. In use, when the distal portion 2 of the catheter and guide wire assembly 1 has been inserted into the artery of a living body and the pressure transducer 4 has, by the connector cable 6, been connected to the external monitor device 7, the momentary blood pressure in the artery can thereby be displayed on the monitor device 7.

Figure 2:
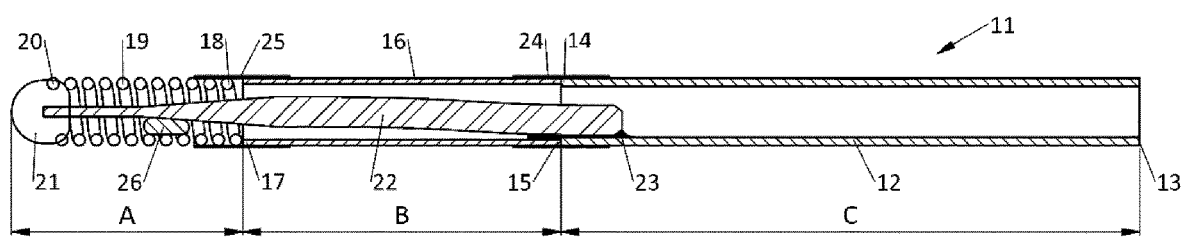
FIG. 2 illustrates schematically a longitudinal cross-section of the catheter and guide wire assembly of FIG. 1.

FIG. 2 shows a longitudinal cross-section of a pressure catheter and guide wire assembly 11, which comprises a tubular shaft 12 having a proximal end 13, which is connectable to an external pressure transducer, as was illustrated and explained in conjunction with FIG. 1, and a distal end 14, which is secured to a proximal end 15 of a tubular extension 16, whose distal end 17 is secured to a proximal end 18 of a helical coil 19, whose distal end 20 is secured in a blunt distal tip 21. The square cut end 14, adjacent to a square cut end 15, is held together and preferably sealed by means of a heat shrink 24. The heat shrink 24, preferably made in polyester, has a wall thickness of about 0.007 mm and length of about 2-10 mm. Due to these small sizes and the softness of the material preferably used, the heat shrink 24 will not add significantly to the overall bending resistance. This type of joint enables or at least facilitates a continuous and large inner lumen as opposed to overlapping joints used in prior art. The heat shrink 24 is also very flexible, which allows bending of the pressure catheter and guide wire assembly 11 without compromising the sealing function of the heat shrink 24. The same type of joint is used between the distal end 17 of the tubular extension 16 and the proximal end 18 of the helical coil 19 by means of a second heat shrink 25. The pressure catheter and guide wire assembly 11 comprises further a core member 22, which is attached, e.g. by soldering or more preferably by gluing, e.g. with use of epoxy, cyanoacrylates or polyurethanes, in a distal portion 23 of the tubular shaft 12 and extends through the tubular extension 16 and the helical coil 19, and is secured in the tip 21. In order to even further secure the core member 22 to the helical coil 19, a joint 26 is made by e.g. soldering or gluing. The outer diameter of the pressure catheter and guide wire assembly 11 is about 0.014 inches (about 0.35 mm), which is a standard dimension within the field. The tubular shaft 12 comprises a hollow and relatively stiff tube made from, e.g., stainless steel, and has length in the interval of about 1200 mm to about 2000 mm, and an inner diameter in the interval of about 0.21 mm to about 0.30 mm. The tubular extension 16 comprises a hollow and relatively flexible, i.e. having a relatively low bending stiffness, tube made from, e.g., polyimide, polyamide or polyurethane, or any compounds thereof, and has a length in the interval of about 120 mm to about 500 mm, and an inner diameter in the interval of about 0.23 mm to about 0.31 mm. The helical coil 19 comprises a flexible and hollow coil made from, e.g., platinum, palladium or tungsten, or any alloys thereof, and has a length in the interval of about 15 mm to about 45 mm and an inner diameter in the interval of about 0.16 mm to about 0.27 mm. The helical coil 19 is further permeable to blood, such that blood pressure pulses can be transferred to a fluid, e.g. saline, contained in the interior of the catheter and guide wire assembly 11. Due to the permeability of the helical coil 19, some blood may also enter into the lumen of the catheter and guide wire assembly 11 and will then become a part of the fluid passageway for transferring pressure pulses from the distal portion of the catheter and guide wire assembly 11 to the proximal end 13 thereof. The core member 22 is a solid metal wire made from, e.g., stainless steel, or a metal having a modulus of elasticity comparable to or higher than the modulus of elasticity of stainless steel, and has a length in the interval of about 140 mm to about 1045 mm. More specifically, the core member 22 extends only a limited distance into the distal portion 23 of the tubular shaft 12 and can extend from about 5 mm to about 500 mm into the distal portion 23, thereby giving the core member 22 the length interval of about 140-1045 mm. The diameter of the core member 22 can vary along its length, i.e. the core member 22 is a tapered metal wire, and the diameter of the core member 22 can in the distal region of the catheter and guide wire 11, i.e. in the tubular extension 16, taper from about 0.19 mm to about 0.07 mm, and more preferably from about 0.16 mm to about 0.09 mm, while the diameter of the core member 22 can in the middle of the tip region be in the interval of about 0.04 mm to about 0.10 mm, or flattened, as is well known for those skilled in the art. By choosing the dimensions given above for the components of the catheter and guide wire assembly 11, the catheter and guide wire assembly 11 is provided with an open, inner lumen which, when filled with a fluid, e.g. saline, works as a transmission line for pressure pulses, as has been explained above.

In an exemplifying embodiment of a catheter and guide wire assembly, a tubular shaft has a length of about 1590 mm and an inner diameter of about 0.26 mm, a tubular extension has a length of about 280 mm and an inner diameter of about 0.29 mm, a helical coil has a length of about 30 mm and an inner diameter of about 0.23 mm, and a core member has a length of about 327 mm (i.e. the core member extends about 17 mm into the tubular shaft and has further the length of the tubular extension (280 mm) plus the length of the coil (30 mm)) and has a diameter which tapers from about 0.16 mm to about 0.09 mm in the region of the tubular extension and ends in a diameter of about 0.05 mm in the middle of the tip region. All these values are summarized and presented in Table 1. However, as will be thoroughly explained below, lengths and diameters of the different components cannot be combined freely; there is a superior limitation which must be fulfilled.

TABLE 1

Typical dimensions of components in a catheter and guide wire assembly.

| Component | Inner diameters (Core member: Outer diameter) [mm] | | | Length [mm] | | |
|---|---|---|---|---|---|---|
| | Typical | Max | Min | Typical | Max | Min |
| Core member | Tip region: 0.05<br>Distal region taper start: 0.09<br>Distal region taper end: 0.16<br>Proximal cylindric region: 0.16 | Tip region: 0.10<br>Distal region taper start: 0.12<br>Distal region taper end: 0.19<br>Proximal cylindric region: 0.19 | Tip region: 0.04<br>Distal region taper start: 0.07<br>Distal region taper end: 0.11<br>Proximal cylindric region: 0.11 | Tip region: 30<br><br>Distal region taper length: 40<br>Proximal cylindric region: 257<br>Within tubular shaft: 17 | Tip region: 45<br><br>Distal region taper length: 80<br>Proximal cylindric region: 920<br>Within tubular shaft: 500 | Tip region: 15<br><br>Distal region taper length: 20<br>Proximal cylindric region: 105<br>Within tubular shaft: 5 |
| Helical coil | 0.23 | 0.27 | 0.16 | 30 | 45 | 15 |
| Tubular extension | 0.29 | 0.31 | 0.23 | 280 | 500 | 120 |
| Tubular shaft | 0.26 | 0.30 | 0.21 | 1590 | 2000 | 1200 |

A catheter and guide wire assembly according to the present invention should not only comprise an inner lumen which provides a passageway for the transmission of blood pressure pulses from a distal region of the catheter and guide wire assembly to a proximal end thereof, but the catheter and guide wire assembly should also comprise an inner lumen whose dimensions allows efficient flushing out of blood which has entered into this inner lumen. Tests have shown that the force needed to flush blood out of the inner lumen of a catheter and guide wire assembly with the aid of a standard syringe is surprisingly sensitive to the overall flow resistance provided by the dimensions of the components of the catheter and guide wire assembly. In Table 2 three examples of component dimensions are given, and in Table 3 the corresponding flow-resistance indices are given. It should be appreciated that the number of workable combinations are infinite and that the given examples are only provided as a guide for the design of a catheter and guide wire assembly which allows flushing of blood out of the inner lumen with a standard syringe. Fluid flow in a tube is governed by Poiseuille's law and states that the flow resistance is proportional to the length of the tube section divided by the fourth power dependence upon the diameter. When calculating flow resistance for the distal and mid segment as shown in Table 3, the hydraulic diameter is calculated by subtracting inner diameter of the tubular part with the diameter of the core member multiplied by 0.7. Flow measurements on parts with applicable sizes and materials have shown that this factor of 0.7 makes the Poiseuille's law more accurate in predicting flow resistance in this particular case, whereas in regular theory the factor is 1 (one). The tapered regions of the core member as described in Table 1 have been approximated with cylindrical dimensions, which is valid when using short tapered lengths as in our typical dimension example. However, the tapered region shall be integrated in the calculation if a resistance index of higher accuracy is needed.

TABLE 2

Three examples of dimensions for the components in a catheter and guide wire assembly.

| Component | Inner diameters D (Core member: Outer diameter d) [mm] | | | Length [mm] | | |
|---|---|---|---|---|---|---|
| | Typical | High resistance | Non working resistance | Typical | High resistance | Non working resistance |
| Core member | Within tubular extension: 0.16 | Within tubular extension: 0.17 | Within tubular extension: 0.17 | Within tubular shaft: 17 | Within tubular shaft: 17 | Within tubular shaft: 80 |
| Tubular extension | 0.29 | 0.27 | 0.27 | 280 | 280 | 280 |
| Tubular shaft | 0.26 | 0.25 | 0.25 | 1590 | 1590 | 1590 |

TABLE 3

Total resistance indices for the three examples of Table 2 above.

| Section of assembly | Assembly | | |
|---|---|---|---|
| | Typical | High resistance | Non working resistance |
| Within tubular extension $L/(D-0,7*d)^4$ | 278 919 | 538 580 | 538 580 |
| Within tubular shaft $L/(D-0,7*d)^4$ | 35 433 | 57 725 | 271 647 |
| Proximal Tubular shaft $L/D^4$ | 347 939 | 407 040 | 407 040 |
| Total resistance index $\Sigma$ (Sections) $[mm^{-3}]$ | 662 291 | 1 003 345 | 1 217 267 |

From Table 2 and Table 3 it should be noted that a total resistance index above about $1.22 \times 10^6$ mm$^{-3}$ does not allow for an efficient flushing of blood out of the inner lumen. A catheter and guide wire assembly according to the invention is therefore characterized by having a total flow-resistance index below about $1.2 \times 10^6$ mm$^{-3}$, and more preferably below about $1.0 \times 10^6$ mm$^{-3}$, and even more preferably below about $0.7 \times 10^6$ mm$^{-3}$. Here it should also be appreciated that a catheter and guide wire assembly can have different structural composition, with different sections comprising different outer members having different dimensions, and an inner, more rigid member having sections with different dimensions, the important feature of such a catheter and guide wire is, however, still that the total flow-resistance index is below about $1.2 \times 10^6$ mm$^{-3}$.

As stated above, a catheter and guide wire assembly should not only provide an efficient and reliable transmission line for pressure pulses and also provide for efficient flushing of blood out of the inner lumen, the catheter and guide wire assembly must at the same time be able act as guide wire which is able to steer through the sometimes very tortuous coronary artery. A catheter and guide wire assembly must therefore have a rather low bending stiffness in the tip region, which continuously increases to a medium bending stiffness and a high torsional rigidity in the distal region and finally a high bending stiffness and a high torsional rigidity in the proximal region. In Table 4 the bending resistance and torsional resistance are given for each region of an exemplifying catheter and guide wire assembly according to the invention. It should however be noted that the dimensions of the embodiment presented in Table 4 are the same as the dimensions that gave the lowest total flow-resistance index in Table 3. For embodiments with a higher total flow-resistance index, which is still at least below $1.2 \times 10^6$ mm$^{-3}$, the bending and torsional resistances are relatively easier to design to be higher. Further, the values of the bending and torsional resistances given in Table 4 show that the mechanical characteristics of the catheter and guide wire assembly are sufficient to provide good steerability. The maximum outer diameter is as mentioned before limited by the standard dimension of 0.014 inch (0.36 mm) for the whole device. The tip region needs to be soft enough to avoid that the tip perforates the artery wall and cause dangerous bleeding, and at the same time stiff enough to be able to cross lesions without collapsing. Since just a minor part of the tip region is part of the pressure conductor it may be designed freely with proper mechanical properties. The middle of the tip region should have a bending resistance of preferably 0.01 to 0.95 Nmm$^2$, or even more preferably 0.02 to 0.12 Nmm$^2$. The distal region needs to be soft enough to align to tortuous vessels without causing high forces on the vessel walls which in turn may cause trauma. The distal region needs also to be stiff enough not to collapse when pushing the wire forward in the artery and stiff enough to be able to support a balloon or stent catheter during a PCI procedure. The distal end of the distal region should have a bending resistance of preferably 0.95 to 6 Nmm$^2$, or even more preferably 1 to 3 Nmm$^2$. The proximal end of the distal region and the proximal region needs to be as stiff as possible in order to transmit torque from the hands of the physician to the tip. Here a balance between low flow resistance and high stiffness is needed. The proximal end of the distal region should have a bending resistance of preferably 3 to 13 Nmm$^2$, or even more preferably 5 to 8 Nmm$^2$. The proximal region should have a bending resistance of preferably 65 to 124 Nmm$^2$, or even more preferably 95 to 110 Nmm$^2$.

TABLE 4

Bending resistance and torsional resistance for different sections regions of catheter and guide wire assembly.

| Parameter | Units | In the middle of the Tip region | | Distal end of Distal region | | Proximal end of Distal region | | Proximal region |
|---|---|---|---|---|---|---|---|---|
| | | Core member | Helical coil | Core member | Tubular extension | Core member | Tubular extension | Tubular shaft |
| Outer diameter | mm | 0.05 | — | 0.09 | 0.34 | 0.16 | 0.34 | 0.35 |
| Inner diameter | mm | — | — | — | 0.29 | — | 0.29 | 0.26 |
| Material | — | Stainless steel | Platinum-Tungsten alloy | Stainless steel | Polyimide | Stainless steel | Polyimide | Stainless steel |
| Modulus of elasticity "E" | N/mm$^2$ | 193 000 | Neglible compared to Core member | 193 000 | 2500 | 193 000 | 2 500 | 193 000 |
| Moment of inertia "I" | mm$^4$ | 0.0000003 | " | 0.0000032 | 0.0003088 | 0.0000322 | 0.0003088 | 0.0005123 |
| Torsion constant "J" | mm$^4$ | 0.0000006 | " | 0.0000064 | 0.0006176 | 0.0000643 | 0.0006176 | 0.0010246 |
| Bending resistance E × I | Nmm$^2$ | 0.05921 | " | 0.622 | 0.772 | 6.209 | 0.772 | 98.874 |

TABLE 4-continued

Bending resistance and torsional resistance for different sections regions of catheter and guide wire assembly.

| Parameter | Units | In the middle of the Tip region | | Distal end of Distal region | | Proximal end of Distal region | | Proximal region |
|---|---|---|---|---|---|---|---|---|
| | | Core member | Helical coil | Core member | Tubular extension | Core member | Tubular extension | Tubular shaft |
| Total Bending resistance for each region E × I | Nmm² | 0.06 | " | 1.4 | | 7.0 | | 99 |
| Torsional resistance E × J | Nmm² | 0.118 | " | 1.243 | 1.544 | 12.418 | 1.544 | 197.748 |
| Total Torsional resistance for each region E × J | Nmm² | 0.12 | " | 2.8 | | 14.0 | | 198 |

Optionally, but preferably, for all embodiments of a catheter and guide wire assembly, the walls of an inner lumen have an anti-thrombogenic surface, e.g. a coating with heparin, to prevent the blood from forming clots and thereby facilitating and even enabling the necessary blood removal flushing.

Optionally, but preferably, for all embodiments of a catheter and guide wire assembly, all or some of the outer surfaces have undergone a friction lowering treatment, e.g. a coating with PTFE and/or a hydrophilic surface, as well known in the art.

Although the present invention has been described with reference to specific embodiments, also shown in the appended drawings, it will be apparent to those skilled in the art that many variations and modifications can be done within the scope of the invention as described in the specification and defined with reference to the claims below.

The invention claimed is:

1. A catheter and guide wire assembly for measurement of blood pressure in a living body, comprising components of dimensions, including a tubular shaft, a tubular extension, a helical coil, a distal tip and a core member,
   wherein the tubular shaft has an open proximal end and a distal end, the distal end of the tubular shaft being connected to a proximal end of the tubular extension, the tubular extension having a distal end connected to a proximal end of the helical coil, the helical coil having a distal end secured in the distal tip,
   wherein the core member is attached in a distal portion of the tubular shaft and extends through the distal portion and through the tubular extension and the helical coil and is secured in the distal tip,
   wherein said catheter and guide wire assembly has an outer diameter of about 0.36 mm,
   wherein an interior of said catheter and guide wire assembly comprises different sections, the different sections comprising:
      interiors of the tubular extension and the distal portion of the tubular shaft, in which interiors the core member extends; and
      an interior of the tubular shaft excluding the distal portion of the tubular shaft, wherein the catheter and guide wire assembly includes an open, inner lumen, comprised by said sections and by the helical coil and the core member,
   wherein the tubular shaft has a length of 1200-2000 mm and an inner diameter of 0.21-0.30 mm,
   wherein the tubular extension has a length of 120-500 mm and an inner diameter of 0.27-0.31 mm,
   wherein the core member includes a tapered portion and a non-tapered portion, and an outer diameter of the non-tapered portion is 0.11-0.19 mm,
   wherein the core member extends from about 5 mm to about 500 mm into the distal portion of the tubular shaft,
   wherein the dimensions of each component are chosen such that a sum of the flow resistances of said different sections is less than about $1.0 \times 10^6$ mm$^{-3}$, where the flow resistance of the interior of the tubular shaft is calculated as the length of this section divided by the fourth power of the inner diameter of the section and the flow resistances of the interiors of the distal portion of the tubular shaft and the tubular extension, respectively, are calculated as the respective length of the section divided by the fourth power of the respective inner diameter of the section minus 0.7 times the respective outer diameter of the core member in the section, and
   wherein the catheter and guide wire assembly comprises a tip region, a distal region and a proximal region, wherein the distal region comprises a proximal end and a distal end, and wherein the proximal end of the distal region has a total bending resistance, defined as the sum of the products of modulus of elasticity and moment of inertia of the core member and the tubular extension, of 3 to 13 Nmm².

2. The catheter and guide wire assembly according to claim 1, wherein the proximal end of the distal region has a total bending resistance of 5 to 8 Nmm².

3. The catheter and guide wire assembly according to claim 1, wherein the distal end of the distal region has a total bending resistance, defined as the sum of the products of modulus of elasticity and moment of inertia of the core member and the tubular extension, of 0.95 to 6 Nmm².

4. The catheter and guide wire assembly according to claim 3, wherein the distal end of the distal region has a total bending resistance of 1 to 3 Nmm².

5. The catheter and guide wire assembly according to claim 1, wherein the proximal region has a total bending resistance, defined as the sum of the product of modulus of elasticity and moment of inertia of the tubular shaft, of 65 to 124 Nmm².

6. The catheter and guide wire assembly according to claim 5, wherein the proximal region has a total bending resistance of 95 to 110 Nmm$^2$.

7. The catheter and guide wire assembly according to claim 1, wherein the middle of the tip region has a bending resistance, defined as the product of modulus of elasticity and moment of inertia of the core member, of 0.01 to 0.95 Nmm$^2$.

8. The catheter and guide wire assembly according to claim 7, wherein the middle of the tip region has a bending resistance of 0.02 to 0.12 Nmm$^2$.

9. The catheter and guide wire assembly according to claim 1, wherein the sum of the flow resistances is less than about 0.7×10$^6$ mm$^{-3}$.

10. The catheter and guide wire assembly according to claim 1, wherein the inner lumen has walls which have an anti-thrombogenic surface.

11. The catheter and guide wire assembly according to claim 3, wherein the proximal region has a total bending resistance, defined as the sum of the product of modulus of elasticity and moment of inertia of the tubular shaft, of 65 to 124 Nmm$^2$.

12. The catheter and guide wire assembly according to claim 11, wherein the proximal region has a total bending resistance of 95 to 110 Nmm$^2$.

13. The catheter and guide wire assembly according to claim 3, wherein the middle of the tip region has a bending resistance, defined as the product of modulus of elasticity and moment of inertia of the core member, of 0.01 to 0.95 Nmm$^2$.

14. The catheter and guide wire assembly according to claim 13, wherein the middle of the tip region has a bending resistance of 0.02 to 0.12 Nmm$^2$.

15. The catheter and guide wire assembly according to claim 5, wherein the middle of the tip region has a bending resistance, defined as the product of modulus of elasticity and moment of inertia of the core member, of 0.01 to 0.95 Nmm$^2$.

16. The catheter and guide wire assembly according to claim 15, wherein the middle of the tip region has a bending resistance of 0.02 to 0.12 Nmm$^2$.

17. The catheter and guide wire assembly according to claim 1, wherein the core member extends from 5 mm to 17 mm into the distal portion of the tubular shaft.

18. The catheter and guide wire assembly according to claim 1, wherein the outer diameter of the tapered portion of the core member at the distal end of the tubular extension is from 0.07 mm to 0.12 mm.

19. The catheter and guide wire assembly according to claim 1, wherein the inner diameter of the tubular shaft is smaller than the inner diameter of the tubular extension.

\* \* \* \* \*